United States Patent [19]

Gerhardt et al.

[11] Patent Number: 4,652,585

[45] Date of Patent: Mar. 24, 1987

[54] N-SUBSTITUTED DIAMINOPROPANE/GLUTAMIC ACID REACTION PRODUCTS

[75] Inventors: Werner Gerhardt, Hilden; Herbert Fischer, Duesseldorf; Rudolf Lehmann, Leichlingen; Karlheinz Disch, Haan; Hans T. Leinen, Aachen, all of Fed. Rep. of Germany

[73] Assignee: Henkel Kommanditgesellschaft auf Aktien, Duesseldorf, Fed. Rep. of Germany

[21] Appl. No.: 713,126

[22] Filed: Mar. 15, 1985

[30] Foreign Application Priority Data

Mar. 24, 1984 [DE] Fed. Rep. of Germany ....... 3410956

[51] Int. Cl.$^4$ .................... C07C 101/24; A01N 37/18
[52] U.S. Cl. .................................. 514/563; 562/561; 562/564
[58] Field of Search ................ 562/561, 564; 514/564, 514/563

[56] References Cited

U.S. PATENT DOCUMENTS

| | | | |
|---|---|---|---|
| 3,222,402 | 12/1965 | Cooperman | 260/583 |
| 3,277,156 | 10/1966 | Ishizuka et al. | 260/482 |
| 3,303,213 | 2/1967 | Kalopissis | 562/561 |
| 3,534,032 | 10/1970 | Kalopissis | 562/561 |
| 3,770,807 | 11/1973 | Sumikawa et al. | 260/482 |
| 3,803,223 | 4/1974 | Mazur | 562/561 |
| 3,873,688 | 3/1975 | Kalopissis | 562/561 |
| 3,920,731 | 11/1975 | Naik | 562/561 |
| 3,979,449 | 9/1976 | Hirsbrunner | 562/561 |
| 4,039,565 | 8/1977 | Throckmorton | 562/564 |
| 4,216,238 | 8/1980 | Baker | 562/561 |
| 4,433,977 | 2/1984 | Carrier | 562/561 |
| 4,505,835 | 3/1985 | Sung | 562/561 |

FOREIGN PATENT DOCUMENTS

| | | | |
|---|---|---|---|
| 98625 | 1/1984 | European Pat. Off. | 562/564 |
| 1254635 | 11/1967 | Fed. Rep. of Germany . | |
| 1493991 | 10/1969 | Fed. Rep. of Germany . | |
| 2158562 | 6/1972 | Fed. Rep. of Germany . | |
| 1351793 | 3/1963 | France . | |
| 59-176377 | 10/1984 | Japan | 562/561 |
| 1080218 | 11/1964 | United Kingdom . | |

*Primary Examiner*—Michael L. Shippen
*Attorney, Agent, or Firm*—Ernest G. Szoke; Henry E. Millson, Jr.; Mark A. Greenfield

[57] ABSTRACT

Compounds which are the reaction products of a $C_{12-14}$-alkyl N-substituted 1,3-diaminopropane and glutamic acid or its 5-methyl ester, optionally alkoxylated, and optionally their salts, are useful as antimicrobial agents.

17 Claims, No Drawings

N-SUBSTITUTED DIAMINOPROPANE/GLUTAMIC ACID REACTION PRODUCTS

BACKGROUND OF THE INVENTION

1. Field of the Invention

This invention relates to compounds which are the reaction products of $C_{12\text{-}14}$-alkyl N-substituted 1,3-diaminopropanes with glutamic acid and/or its $C_{1\text{-}4}$-alkyl esters, their alkoxylation products and their salts; as well as the use of these compounds as antimicrobial agents.

2. Statement of the Related Art

N-substituted 1,3-diaminopropanes of the formula:

$$R^1\text{---}NH\text{---}CH_2\text{---}CH_2\text{---}CH_2\text{---}NH_2 \qquad (I)$$

wherein $R^1$ is a $C_{12\text{-}14}$ linear alkyl
are generally known, and may be conventionally synthesized by reacting the corresponding alkylamines with acrylonitrile, followed by hydrogenation [see Houben-Weyl, *Methoden der organischen Chemie*, 4th Ed, G. Thieme Verlag, Stuttgart, F.R. Germany, vol. 11/1, p. 564 (1957) as well as U.S. Pat. No. 3,222,402 and corresponding French Pat. No. 1,351,793]. Specific known compounds include N-n-dodecyl- and N-n-tetradecyl-1,3-diaminopropane.

Glutamic acid is also known, as are its $C_{1\text{-}4}$-alkyl 5-esters, such as ethyl, n-propyl, n-butyl, and methyl. Processes for the production of glutamic acid-5-esters are described in: U.S. Pat. No. 3,277,156 (and corresponding German published application No. 12 54 635); British Pat. No. 1,080,218 (and corresponding German published application No. 14 93 991); as well as in U.S. Pat. No. 3,770,807 (and corresponding German published application No. 21 58 562). The L-glutamic acid 5-methyl ester is available in the United States from Aldrich Chemical Co., Milwaukee, Wisc., among others.

SUMMARY OF THE INVENTION

The compounds of this invention may be synthesized by:
reacting:
(a) N-substituted 1,3-diaminopropanes of the formula

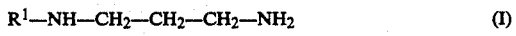

$$R^1\text{---}NH\text{---}CH_2\text{---}CH_2\text{---}CH_2\text{---}NH_2 \qquad (I)$$

wherein $R^1$ is a $C_{12\text{-}14}$-linear alkyl; with
(b) glutamic acid or its ester of the formula

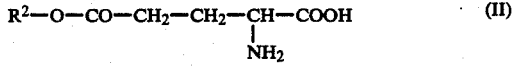

$$R^2\text{---}O\text{---}CO\text{---}CH_2\text{---}CH_2\text{---}\underset{\underset{NH_2}{|}}{CH}\text{---}COOH \qquad (II)$$

wherein $R^2$ is a $C_{1\text{-}4}$-alkyl or H;
the mol ratio of (a) to (b) being 1:1–2, and the reaction preferably being conducted for 0.5 to 10 hours at 60° to 175° C., accompanied by the elimination of alcohol and/or water by-products.

Optionally, the resulting compounds may be further reacted with ethylene oxide or propylene oxide under known alkoxylation conditions.

The reaction products, with or without alkoxylation, may then be further reacted with inorganic or organic acids to form their corresponding salts.

All of the above compounds are useful as microbistatic and/or antimicrobial agents.

Other than in the operating examples, or where otherwise indicated, all numbers expressing quantities of ingredients or reaction conditions used herein are to be understood as modified in all instances by the term "about".

DETAILED DESCRIPTION OF THE INVENTION

The diaminopropanes corresponding to formula I may be used individually or in admixture. N-n-dodecyl-1,3-diaminopropane and N-n-tetradecyl-1,3-diaminopropane are preferred, and their mixture in which the dodecyl is 65 to 75 mol % is most preferred.

The free glutamic acid and the glutamic acid component of the esters may be present in the L-form, in the D-form and in the racemic form, the L-form being the preferred form in both cases. The alcohol component of the glutamic acid-5-esters may consist of aliphatic alcohols containing from 1 to 4 carbon atoms, for example ethanol, n-propanol, n-butanol, preferably methanol.

If free glutamic acid is used as a starting material in the production of the antimicrobial agents according to the invention, the reactants may be allowed to act on one another as such, i.e. in the absence of solvents, and the water formed distilled off. However, it has proved best to carry out the reaction in a suitable organic solvent. The reactants must be sufficiently soluble in the solvent used. At the same time, the solvent must be able to act as an entraining agent for the water to be removed from the reaction mixture. Suitable solvents and entraining agents are straight-chain and branched aliphatic alcohols containing from 4 to 6 carbon atoms, for example isoamyl alcohol, and toluene. In this variant of the process, the mixture of N-alkyl diaminopropane, glutamic acid and solvent is boiled under reflux on a water separator at least until the quantity of water calculated for amide formation has separated off. When the elimination of water has reached the prescribed level, the solvent is distilled off from the reaction mixture, preferably under reduced pressure. The reaction products which are left as residue after the solvent has been distilled off may be directly used, i.e. without further purification, as antimicrobial agents or as starting material in the production of the ethylene oxide or propylene oxide adducts and salts of inorganic and organic acids to which the invention also relates.

If glutamic acid-5-esters and N-alkyl diaminopropanes are used as starting materials the reactants are heated, preferably in the absence of solvents, to temperatures of up to 175° C. until the quantity of alcohol calculated for amide formation has been distilled off. The desired reaction products are directly obtained in this way. They may be used without further purification as antimicrobial agents or as starting material in the production of salts or alkylene oxide adducts.

Where the compounds according to the invention are produced from N-alkyl diaminopropanes and glutamic acid, products of high antimicrobial activity are also obtained when the elimination of water goes considerably beyond the quantity calculated for the formation of carboxylic acid amide. The water additionally formed apparently emanates from intermolecular or intramolecular reactions of which the nature is not known at the present time. Comparable products are also obtained if, in the reaction of glutamic acid-5-esters with the N-alkyl diaminopropanes, the products obtained during elimination of the alcohol are heated to temperatures of from 100° to 175° C. Prolonged heating to temperatures above 175° C. give products having impaired performance properties.

The further reaction of the above diamine/glutamic reaction products with ethylene oxide and/or propylene oxide is carried out in known manner at 50° to 150° C. For efficiently producing the alkylene oxide adducts, it has proven to be best to carry out the addition reaction immediately after formation of the diamine/glutamic reaction products. The quantitative ratio between the reactants is selected so that the mol ratio of the N-substituted diaminopropane on which the reaction product is based to the ethylene oxide or propylene oxide is 1:1–10, preferably 1:1. The products resulting from the alkoxylation step may be used without further purification as antimicrobial agents or as a starting material in the production of salts with inorganic or organic acids.

Any of the above compounds may be reacted with at least one inorganic or organic acid to form the corresponding salt. Suitable acids are hydrochloric, sulfuric, phosphoric, formic, acetic, lactic, tartaric, citric, and benzoic. The salts may be produced by dissolving the alkoxylated or non-alkoxylated reaction products in water in a suitable concentration, for example 10% by weight, and neutralizing the solution obtained with an aqueous solution of the particular acid selected until the required neutral pH-value is reached. Unless the aqueous solutions of the salts obtained are directly used, the anhydrous salts may be obtained from them by evaporating the water. In certain cases, it may be best to dissolve the diamine/glutamic reaction products in a suitable organic solvent, for example ethyl-acetate, and to neutralize the solution obtained with a solution of the particular acid selected in that solvent. In this case, too, the salts may be obtained as such by evaporating the solvent.

USES OF THE INVENTION COMPOUNDS

By virtue of their microbistatic and microbicidal effect on bacteria and fungi, the compounds according to the invention are suitable for performing a variety of disinfecting and preserving functions in the non-therapeutic field. Where they are used as active ingredients of antimicrobial preparations, the compounds according to the invention may be incorporated in liquid, paste-form or solid preparations. Preparations such as these may be used in a variety of fields, for example as cleaning, disinfecting and preserving agents for textiles, floors, hospital equipment, medical instruments, schools, swimming pools, public transport vehicles and commercial installations, such as dairies, breweries and laundries.

In addition to the active ingredients described in the foregoing, the antimicrobial preparations generally contain other constituents of the type normally used which are selected according to the particular formulation and application envisaged. Suitable solvents for liquid formulations are water and standard organic solvents, particularly alcohols and glycol ethers, optionally in admixture with water. If, in addition to the antimicrobial effect, it is desired to obtain a cleaning effect, the preparations may contain nonionic surfactants or amphoteric surfactants. Suitable nonionic surfactants are adducts of from 4 to 40 mols and preferably from 4 to 20 mols of ethylene oxide with 1 mole of fatty alcohol, alkyl cyclohexanol, alkyl phenol, fatty acid, fatty amine, fatty acid amide or alkane sulfonamide. Particular interest is attributed to adducts of from 5 to 16 mols of ethylene oxide with coconut oil or tallow fatty alcohols, oleyl alcohol and mono-, di- or trialkyl phenols and with monoalkyl cyclohexanols containing from 6 to 14 carbon atoms in the alkyl radicals. Suitable amphoteric surfactants are the derivatives of secondary or tertiary aliphatic amines, the aliphatic radicals being linear or branched and one radical containing from 8 to 18 carbon atoms and another containing a solubilizing anionic group, such as carboxy, sulfo, sulfato, phosphato or phosphono.

The antimicrobial preparations may also contain builders. Suitable builders are inorganic or organic salts, particularly inorganic or organic complexing agents. Builders which may be used include ortho-, pyro- and tripolyphosphates of the alkali metals, alkali salts of complexing aminocarboxylic acids, such as nitrilo triacetic acid and ethylene diamine tetraacetic acid, alkali salts of complexing phosphonic acids, such as 1-hydroxyethane-1,1-diphosphonic acid, aminotrimethylene phosphonic acid and ethylene diamine tetramethylene phosphonic acid, and also alkali salts of sulfodicarboxylic acids, lactic acid, citric acid and tartaric acid. Other suitable builders are the acidic water-soluble salts of relatively high molecular weight polycarboxylic acids, for example polymers of maleic acid, itaconic acid, fumaric acid and citraconic acid. Copolymers of these acids with one another or with other polymerizable compounds, such as ethylene, propylene, acrylic acid, vinyl acetate, isobutylene, acrylamide and styrene, may also be used. If the antimicrobial preparations contain organic solvents, it may be advisable to add solution promoters, such as benzene, toluene and xylene sulfonic acid in the form of their alkali salts.

The content of compounds according to the invention in the antimicrobial preparations ready for use amounts to between 0.01 and 5% by weight, based on the preparation as a whole. For producing preparations such as these ready for use, it is possible to make up concentrates or solid mixtures containing up to 50% by weight of active ingredient.

In addition, the compounds according to the invention may be used for preserving technical products susceptible to bacterial and fungal attack and to other forms of microbial infestation, for example pastes, glues, emulsion paints and drilling and cutting oils. For this particular application, additions of from 0.01 to 2% by weight, based on the material to be preserved, are generally sufficient.

EXAMPLES 1–16 (REACTION PRODUCTS)

EXAMPLE 1

501.8 g (2 mols) of dodecyl/tetradecyl 1,3-diaminopropane (70 mol % of dodecyl and 30 mol % of tetradecyl 1,3-diaminopropane) and 322.3 g (2 mols) of L-glutamic acid-5-methyl ester were heated with stirring for 6 hours to a maximum temperature of 133° C. (sump), the methanol formed at 95° to 100° C. (sump) being distilled off. On completion of the reaction, residues of methanol were removed from the reaction mixture by briefly applying a weak vacuum (150 to 50 mbars) and at the same time stirring, leaving as residue 735.8 g (97% of the theoretical) of a reaction product of dodecyl/tetradecyl propylene diamine and L-glutamic acid-5-methyl ester in a molar ratio of 1:1 (substance A) in the form of a beige paste melting at 80° to 90° C.

$C_{20.6}H_{42.2}N_3O_3$ (MS 379.99) Analysis: Calculated (%): 65.12 C; 11.20 H; 11.06 N; 12.63 O. Found (%): 65.2 C; 11.0 H; 11.4 N; 12.4 O.

IR (film, cm$^{-1}$): 3150–3500 (broad), 2925 (s), 2855 (s), 1675 (s) 1590 (m), 1467 (w), 1403 (w), 1295 (w).

EXAMPLE 2

251 g (1 mol) of dodecyl/tetradecyl 1,3-diaminopropane (70/30 mol %) were reacted with 177 g (1.1 mol) of L-glutamic acid-5-methyl ester in the same way as in Example 1. The reaction product of dodecyl/tetradecyl 1,3-diaminopropane and L-glutamic acid-5-methyl ester in a molar ratio of 1:1.1 (substance B) was obtained in a yield of 88% of the theoretical; beige paste melting at 96° to 100° C.

EXAMPLE 3

125.9 g (0.5 mol) of dodecyl/tetradecyl 1,3-diaminopropane (70/30 mol %) and 73.6 g (0.5 mol) of L-glutamic acid were heated for 5 hours to 175° C. (sump) in a flask with an attached distillation bridge. Most of the water expected during amide formation was given off with vigorous foaming at 135° to 145° C. (sump). A total of 9 ml of water was distilled off during the reaction, leaving as residue 182 g (95.8% of the theoretical) of a reaction product of dodecyl/tetradecyl 1,3-diaminopropane and L-glutamic acid in a molar ratio of 1:1 (substance C) in the form of a pale beige paste.

EXAMPLE 4

A mixture of 25.1 g (0.1 mol) of dodecyl/tetradecyl 1,3-diaminopropane (70/30 mol %), 14.7 g (0.1 mol) of L-glutamic acid and 100 ml of i-amyl alcohol as solvent and entraining agent was boiled under reflux with stirring on a water separator until substantially the calculated quantity of water had separated off (about 2 hours). The maximum sump temperature amounted to 146° C. Thereafter, most of the i-amyl alcohol was distilled off in a water jet vacuum and the rest in an oil pump vacuum, leaving as residue 36.1 g (95% of the theoretical) of a reaction product of dodecyl/tetradecyl 1,3-diaminopropane and L-glutamic acid in a molar ratio of 1:1 (substance D) in the form of a yellowish paste melting at 72° to 82° C.

$C_{20.6}H_{42.2}N_3O_3$ (MW 379.99) Analysis: Calculated (%): 65.12 C; 11.20 H; 11.06 N; 12.63 O. Found (%): 65.3 C; 11.0 H; 11.0 N; 12.4 O.

IR (film, cm$^{-1}$): 3150–3350 (broad), 2925 (s) 2855 (s), 1675 (s), 1592 (m), 1467 (w), 1400 (w), 1290 (w).

EXAMPLE 5

38.0 g (0.1 mol) of the reaction product of dodecyl/tetradecyl 1,3-diaminopropane and L-glutamic acid-5-methyl ester in a molar ratio of 1:1 (substance A of Example 1), dissolved in 100 ml of isopropanol, were reacted in an autoclave for 2 hours at 100° C. with 4.4 g (0.1 mol) of ethylene oxide. Removal of the solvent from the reaction mixture by distillation left 42.5 g (100% of the theoretical) of the corresponding ethylene oxide adduct (substance E) in the form of a clear, yellowish, viscous paste softening at 40° to 45° C.

$C_{22.6}H_{46.2}N_3O_4$ (MW 424.04) Analysis: Calculated (%): 64.02 C; 10.98 H: 9.91 N. Found (%): 64.7 C; 11.1 H; 9.7 N.

IR (film, cm$^{-1}$): 3270 (broad), 2930 (s), 2860 (s), 1685 (s), 1599 (m), 1466 (w), 1400 (w), 1290 (w).

EXAMPLE 6

38.0 g (0.1 mol) of the reaction product of dodecyl/tetradecyl 1,3-diaminopropane and L-glutamic acid-5-methyl ester in a molar ratio of 1:1 (substance A of Example 1) were reacted with 8.8 g (0.2 mol) of ethylene oxide in the same way as in Example 5. The corresponding ethylene oxide adduct (substance F) in the form of a beige paste was obtained in a yield of 46.8 g (100% of the theoretical).

EXAMPLE 7

38.0 g (0.1 mol) of the reaction product of dodecyl/tetradecyl 1,3-diaminopropane and L-glutamic acid-5-methyl ester in a molar ratio of 1:1 (substance A of Example 1) were reacted with 17.6 g (0.4 mol) of ethylene oxide in the same way as in Example 5. The corresponding ethylene oxide adduct (substance G) in the form of a brown liquid ($n_D^{20}=1.4917$) was obtained in a yield of 48.9 g (88% of the theoretical).

EXAMPLE 8

38.0 g (0.1 mol) of the reaction product of dodecyl/tetradecyl 1,3-diaminopropane and L-glutamic acid-5-methyl ester in a molar ratio of 1:1 (substance A of Example 1) were reacted with 44 g (1.0 mol) of ethylene oxide in the same way as in Example 5. The corresponding ethylene oxide adduct (substance H) in the form of a red-brown liquid ($n_D^{20}=1.4791$) was obtained in a yield of 82 g (100% of the theoretical).

EXAMPLE 9

38.0 g (0.1 mol) of the reaction product of dodecyl/tetradecyl 1,3-diaminopropane and L-glutamic acid-5-methyl ester in a molar ratio of 1:1 (substance A of Example 1) were reacted with 5.8 g (0.1 mol) of propylene oxide in the same way as in Example 5. The corresponding propylene oxide adduct (substance I) in the form of a yellow, viscous oil was obtained in a yield of 42.9 g (98% of the theoretical).

EXAMPLE 10

A mixture 9.77 g (0.04 mol) of dodecyl/tetradecyl 1,3-diaminopropane (70/30 mol %) and 12.5 g (0.08 mol) of L-glutamic acid-5-methyl ester was gradually heated with stirring to 170° C. (sump). The methanol formed at 130°–140° C. (sump) was distilled off. On completion of the reaction, residues of methanol were removed in vacuo, leaving as residue 14.0 g (71% of the theoretical) of the reaction product of dodecyl/tetradecyl 1,3-diaminopropane and L-glutamic acid-5-methyl ester in a molar ratio of 1:2 (substance J) in the form of a pale beige paste melting at 90° to 100° C.

$C_{25.6}H_{49.2}N_4O_6$ (MW 509.1) Analysis: Calculated (%): 60.40 C; 9.74 H; 11.1 N. Found (%): 60.6 C; 9.48 H; 11.0 N.

IR (film in cell, CHCl$_3$, cm$^{-1}$): 3250 (broad), 2930 (s), 2860 (m), 1670–1680 (s, broad), 1590–1600 (m), 1396 (w), 1183 (m).

EXAMPLE 11

A mixture of 125.9 g (0.5 mol) of dodecyl/tetradecyl 1,3-diaminopropane (70/30 mol %) and 147.1 g (1 mol) of L-glutamic acid was gradually heated over a period of 5 hours to 175° C. (sump). The water formed during the reaction was distilled off. Most of the water expected during amide formation was given off at 145° to 155° C. (sump), leaving as residue 240 g (94% of the theoretical) of the reaction product of dodecyl/tetradecyl 1,3-diaminopropane and l-glutamic acid in a molar ratio of 1:2 (substance K) in the form of a brown, glass-like substance melting at 55° C.

EXAMPLE 12

A mixture of 62.7 g (0.25 mol) of dodecyl/tetradecyl 1,3-diaminopropane (70:30 mol %), 73.6 g (0.5 mol) of L-glutamic acid and 100 ml of i-amyl alcohol as solvent and entraining agent was refluxed with stirring on a water separator until the calculated quantity of water had separated off (about 2 hours). The maximum sump temperature amounted to 135° C. Thereafter, most of the i-amyl alcohol was distilled off in a water jet vacuum and the rest in an oil pump vacuum, leaving as residue 124.9 g (98.1% of the theoretical) of the reaction product of dodecyl/tetradecyl 1,3-diaminopropane and L-glutamic acid in a molar ratio of 1:2 (substance L) in the form of a yellow, glass-like substance melting at 90° to 100° C.

EXAMPLE 13

A solution of 10 g of the reaction product of dodecyl/tetradecyl 1,3-diaminopropane and L-glutamic acid-5-methyl ester in a molar ratio of 1:1 (substance A of Example 1) in 30 ml of water was adjusted to pH 7 with dilute acetic acid. The solution was stirred for 10 minutes and then concentrated by evaporation to dryness, leaving as residue the corresponding acetate (substance M) in the form of a beige paste melting at 65° to 70° C.

EXAMPLE 14

A solution of 10 g of the reaction product of dodecyl/tetradecyl 1,3-diaminopropane and L-glutamic acid-5-methyl ester in a molar ratio of 1:1 (substance A of Example 1) in 30 ml of water was adjusted to pH 7 with dilute hydrochloric acid. The solution was stirred for 10 minutes and then concentrated by evaporation to dryness, leaving as residue the corresponding hydrochloride (substance N) in the form of a colorless, hydroscopic salt.

EXAMPLE 15

A solution of 10 g of the reaction product of dodecyl/tetradecyl 1,3-diaminopropane and L-glutamic acid in a molar ratio of 1:1 (substance D of Example 4) in 30 ml of water was adjusted to pH 6.5 with dilute phosphoric acid. The solution was stirred for 10 minutes and then concentrated by evaporation to dryness, leaving as residue the corresponding phosphate (substance O) in the form of a colorless salt.

EXAMPLE 16

A solution of 10 g of the reaction product of dodecyl/tetradecyl 1,3-diaminopropane and L-glutamic acid-5-methyl ester in a molar ratio of 1:1 (substance A of Example 1) in 100 ml of ethyl acetate was adjusted to pH 7 with a 1-molar benzoic acid solution in ethyl acetate. Removal of the solvent by distillation left as residue the corresponding benzoate (substance P) in the form of a highly viscous oil.

EXAMPLES 17–19 (ANTIMICROBIAL ACTIVITY)

EXAMPLE 17

The microbistatic activity of substances A to P according to the invention was tested on the following test germ suspensions:

| | |
|---|---|
| 1. Staphylococcus aureus | $2 \times 10^9$ germs/ml |
| 2. Escherichia coli | $2 \times 10^9$ germs/ml |
| 3. Pseudomonas aeruginosa | $5 \times 10^8$ germs/ml |
| 4. Candida albicans | $2 \times 10^8$ germs/ml |
| 5. Aspergillus niger | $5 \times 10^7$ germs/ml |
| 6. Penicillium camerunense | $5 \times 10^7$ germs/ml |

The inhibiting concentrations of the compounds to be tested was determined by the dilution test as laid down in the guidelines for testing chemical disinfectants of the Deutsche Gesellschaft fur Hygiene und Mikrobiologie (1972). The tests were carried out in sterile test tubes containing Standard-I-Bouillon (Merck, pH 7.5) (standard-I-broth) or Wurze-Bouillon (Merck, pH 5.5) (malt broth). After the active substances had been added, the volume of nutrient solution in the tubes amounted to 5 ml in each case. Quantities of 0.1 ml of the test germ suspensions in the concentrations indicated were then introduced into the test tubes. The nutrient solution samples inoculated with bacteria were stored in an incubator for 3 days at 37° C. The samples inoculated with fungi were incubated for 4 days at 30° C. Thereafter, the concentration of active substance added to the nutrient medium which had still just inhibited the growth of the germs was determined. The value determined in this way was termed the inhibiting concentration. The following active substance concentrations in ppm were tested: 1000, 500, 250, 100, 50 and 10.

The inhibiting concentrations set out in Table I below were determined for substances A to P.

TABLE I

| | Inhibiting concentrations (in ppm) of substances A to P in the dilution test | | | | | |
|---|---|---|---|---|---|---|
| | Test germ | | | | | |
| Substance | 1 | 2 | 3 | 4 | 5 | 6 |
| A | ≦10 | ≦10 | 50 | ≦10 | 100 | 100 |
| B | ≦10 | ≦10 | 50 | 100 | 500 | 100 |
| C | ≦10 | ≦10 | ≦10 | 100 | 250 | 100 |
| D | ≦10 | ≦10 | 50 | 250 | 500 | 250 |
| E | ≦10 | 50 | 50 | 250 | 500 | 250 |
| F | ≦10 | ≦10 | 500 | 250 | 500 | 250 |
| G | 50 | 50 | 250 | 500 | 500 | 250 |
| H | 50 | 50 | >1000 | 1000 | 500 | 500 |
| I | ≦10 | ≦10 | 100 | 250 | 500 | 250 |
| J | ≦10 | 50 | 50 | 250 | 500 | 250 |
| K | 50 | 50 | 500 | 500 | 500 | 250 |
| L | ≦10 | ≦10 | ≦10 | 250 | 500 | 500 |
| M | ≦10 | ≦10 | ≦10 | 50 | 100 | 100 |
| N | ≦10 | ≦10 | ≦10 | 250 | 500 | 250 |
| O | ≦10 | 50 | 50 | 250 | 1000 | 500 |
| P | ≦10 | ≦10 | 50 | 100 | 250 | 250 |

EXAMPLE 18

The microbicidal activity of substances A to P according to the invention was tested on the following test germ suspension:

| | |
|---|---|
| 1. Staphylococcus aureus | $2 \times 10^9$ germs/ml |
| 2. Escherichia coli | $2 \times 10^9$ germs/ml |
| 3. Pseudomonas aeruginosa | $5 \times 10^8$ germs/ml |

-continued

| | | |
|---|---|---|
| 4. *Candida albicans* | $2 \times 10^8$ | germs/ml |
| 5. *Asperigillus niger* | $5 \times 10^7$ | germs/ml |
| 6. *Penicillium camerunense* | $5 \times 10^7$ | germs/ml |

The destruction times of the products to be tested were determined by the suspension test as laid down in the guidelines for testing chemical disinfectants of the Deutsche Gesellschaft für Hygiene und Mikrobiologie (1972). The compounds to be tested were first dissolved in a little alcohol. Test solutions containing 3000 ppm and 500 ppm of active ingredient and at most 1% by weight of ethanol were prepared from the ethanolic solutions by dilution with hard water (hardness=17° dH -German hardness). Quantities of 0.1 ml of the test germ suspensions were pipetted into test tubes at room temperature. Quantities of 10 ml of the test solutions described above were then added. After different contact times of up to 120 minutes at room temperature, 0.1 ml of material was removed from the test tubes using a pipette and inoculated into 10 ml of nutrient solution containing 3% of surfactant (Tween 80, a product of ICI Americas, Inc.) and 0.3% of lecithin as deinhibitors. The nutrient medium consisted of 2.5% by weight Standard-I-Bouillon (Merck) (standard-I-broth) for germs 1 to 3 and of Wurze-Bouillon (Merck, pH 5.5) (malt broth). The samples were incubated at 37° C. and 30° C. After 3 days at the earliest, the cultures were macroscopically assessed for growth and the destruction times determined in this way. They are shown in Table II below.

TABLE II

Destruction times (in mins.) of substances A to P in the suspension

| Substances | Conc. (ppm) | Test Germ 1 | 2 | 3 | 4 | 5 | 6 |
|---|---|---|---|---|---|---|---|
| A | 3000 | ≦15 | ≦15 | ≦15 | ≦15 | ≦15 | ≦15 |
|   | 500  | ≦15 | ≦15 | ≦15 | ≦15 | >120 | ≦15 |
| B | 3000 | ≦15 | ≦15 | ≦15 | ≦15 | 60 | ≦15 |
|   | 500  | ≦15 | ≦15 | 120 | ≦15 | 120 | 60 |
| C | 3000 | ≦15 | ≦15 | ≦15 | ≦15 | 60 | ≦15 |
|   | 500  | ≦15 | ≦15 | ≦15 | ≦15 | 60 | >120 |
| D | 2000 | ≦15 | ≦15 | ≦15 | ≦15 | 60 | ≦15 |
|   | 500  | ≦15 | ≦15 | ≦15 | ≦15 | 60 | ≦15 |
| E | 3000 | ≦15 | ≦15 | ≦15 | ≦15 | >120 | 60 |
|   | 500  | 60 | ≦15 | 120 | 120 | >120 | 120 |
| F | 3000 | ≦15 | ≦15 | >120 | ≦15 | >120 | >120 |
|   | 500  | ≦15 | 60 | — | ≦15 | — | — |
| G | 3000 | ≦15 | ≦15 | ≧120 | 60 | >120 | >120 |
|   | 500  | 60 | >120 | — | >120 | — | — |
| H | 3000 | 60 | >120 | >120 | >120 | >120 | >120 |
|   | 500  | >120 | — | — | — | — | — |
| I | 3000 | ≦15 | ≦15 | ≦15 | ≦15 | >120 | 120 |
|   | 500  | ≦15 | ≦15 | ≦15 | ≦15 | >120 | >120 |
| J | 3000 | 60 | ≦15 | ≦15 | 60 | >120 | >120 |
|   | 500  | 120 | ≦15 | 60 | 120 | >120 | >120 |
| K | 3000 | 60 | >120 | ≦15 | 120 | >120 | >120 |
|   | 500  | 60 | >120 | ≧120 | >120 | >120 | >120 |
| L | 3000 | 60 | ≦15 | ≦15 | ≦15 | >120 | >120 |
|   | 500  | 60 | ≦15 | ≦15 | 60 | — | — |
| M | 3000 | 60 | ≦15 | ≦15 | ≦15 | 120 | 120 |
|   | 500  | 120 | 60 | ≦15 | >120 | — | — |
| N | 3000 | 60 | ≦15 | ≦15 | 60 | >120 | >120 |
|   | 500  | 60 | ≦15 | ≦15 | 60 | >120 | >120 |
| O | 3000 | 60 | ≦15 | ≦15 | 60 | >120 | >120 |
|   | 500  | 120 | ≦15 | ≦15 | 60 | >120 | >120 |
| P | 3000 | 120 | ≦15 | ≦15 | 60 | >120 | >120 |
|   | 500  | 120 | ≦15 | ≦15 | 120 | >120 | >120 |

EXAMPLE 19

The antimicrobial activity of substances A, B, C, E, J, and M according to the invention in surface disinfection was determined by the scrubbing disinfection test. This test was taken from the guidelines for testing chemical disinfectants as published by the Deutsche Gesellschaft für Hygiene und Mikrobiologie (1959). 6×6 cm large pieces of painted wooden plates and PVC floor tiles were used as models of contaminated surfaces. Suspensions of *Staphylococcus aureus* containing $2 \times 10^9$ germs/ml and of *Candida albicans* containing $5 \times 10^8$ germs/ml were used for contaminating the surfaces. Quantities of 0.1 ml of the germ suspension were pipetted onto each test surface and uniformly distributed by means of a glass spatula. After the germ suspension had been dried, the test surfaces were uniformly wetted with the disinfection solution using an absorbent cotton swab.

Concentrates of the following composition were used for preparing the disinfection solutions:
10% by weight of active ingredient (substances A, B, C, E, J and M)
10% by weight of nonylphenol+9.5 moles of ethylene oxide
40% by weight of ethanol
40% by weight of water For application, these concentrates were diluted with water in a ratio of 1:50.

After contact times of 1,2,4 and 6 hours, one quadrant of each of the treated surfaces was wiped with sterile absorbent cotton swabs which had been moistened by brief immersion in broth. The swabs were wiped over broth agar plates (Merck Standard-I-Bouillon+3% by weight of surfactant (Tween 80, a product of ICI Americas, Inc.)+0.3% by weight of lecithin+0.1% by weight of histidine for *Staphylococcus aureus* and Wurze-Bouillon+3% by weight of surfactant (Tween ® 88)+0.3% by weight of lecithin+0.1% by weight of histidine for *Candida albicans*). The agar plates were incubated for 48 hours at 30° C.

The results obtained on evaluation are shown in Table III below.

TABLE III

Destruction times (in hours) of substances A, B, C, E, J and M in surface disinfection

| | | Staph. aureus | | Candida albicans | |
|---|---|---|---|---|---|
| Substance | pH | wood | PVC | wood | PVC |
| A | 8.3 | 1 | 1 | 1 | 1 |
| B | 8.4 | 2 | 2 | 1 | 1 |
| C | 9.9 | 4 | 4 | 2 | 1 |
|   | 10.4 | 6 | 6 | 1 | 4 |
| E | 8.4 | ++ | ++ | 2 | 4 |
| J | 7.5 | + | 6 | 4 | 1 |
|   | 8.5 | ++ | ++ | 4 | 4 |
|   | 9.9 | +++ | +++ | 1 | 2 |
| M | 4.8 | ++ | ++ | 2 | 2 |
| CH$_2$O | — | 6 | 6 | 1 | 1 |

+ = <50 germs remaining per quadrant
++ = 50-200 germs remaining per quadrant
+++ = >200 germs remaining per quandrant

EXAMPLE 20 (TOXICOLOGY)

Substance M of Example 15 was selected for an informative study of the toxicological properties of the substances according to the invention.

With oral administration to mice, the acute toxicity $LD_{50}$ amounted to more than 3125 mg/kg. The substance did not produce any symptoms.

Skin compatability was tested on hairless mice. To this end, 0.5% by weight solutions of the active substance were each applied twice daily for 5 successive days to the same areas of skin. The treated animals did not show any reaction.

EXAMPLE 21 (PREPARATIONS)

Some preparations containing the substances according to the invention are shown in the following (PBW=parts by weight):

I. Bath Foam

15 PBW bis-(2-hydroxyethyl)-coconut oil fatty acid amine oxide (50% by weight of washing-active substance)
20 PBW of coconut oil fatty acid amidopropyl dimethylaminoacetic acid betaine
5 PBW coconut oil fatty acid ethanolamide
0.5 PBW substance A
59.5 PBW water Substances G, K and M may be used equally effectively instead of substance A.

II. Deodorant Spray

10 PBW octyl dodecanol
1 PBW perfume oil
2 PBW substance B
87 PBW ethanol
100 PBW propellent gas Substances H, I, L and P may be used equally effectively instead of substance B.

III. Disinfecting Handwashing Paste

25 PBW coconut oil fatty acid amidopropyl dimethylaminoacetic acid betaine
3 PBW coconut oil fatty acid ethanolamide
43 PBW marble dust
2 PBW substance D
27 PBW water Substances F and O may be used equally effectively instead of substance D in this formulation.

IV. Disinfecting Cleaner for Hard Surfaces

13 PBW $C_{10}$-$C_{12}$-fatty alcohol+12 EO
10 PBW substance C
5 PBW nitrilotriacetic acid, Na-salt
10 PBW isopropanol
62 PBW water Substances E, J and N may be used equally effectively instead of substance C.

We claim:

1. A compound which is
(A) the reaction product of:
  (a) at least one $C_{12-14}$-alkyl N-substituted 1,3-diaminopropane; with
  (b) at least one of glutamic acid or its $C_{1-4}$-alkyl 5-ester; the mol ratio of a:b being 1:1-2;
(B) the alkoxylation product of (A) with ethylene oxide or propylene oxide in a mol ratio of said diaminopropane to said alkylene oxide of 1:1-10; or
(C) the salt of (A) or (B) with an organic or inorganic acid.

2. The compound of claim 1 in the form of its salt with an organic or inorganic acid.

3. A compound which is
(A) the reaction product of:
  (a) at least one diaminopropane of the formula:

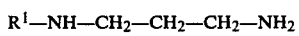
$R^1$—NH—$CH_2$—$CH_2$—$CH_2$—$NH_2$ wherein: $R^1$ is a $C_{12-14}$-linear alkyl; with
  (b) at least one glutamic acid or its ester of the formula:

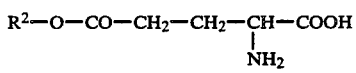
$$R^2-O-CO-CH_2-CH_2-\underset{NH_2}{CH}-COOH$$

wherein: $R^2$ is a $C_{1-4}$-alkyl or H; the mole ratio of a:b being 1:1-2, and the reaction being conducted for about 0.5 to 10 hours at about 60° to 175° C., accompanied by the elimination of alcohol and/or water by-products;
(B) the alkoxylation product of (A) with ethylene oxide or propylene oxide in a mol ratio of said diaminopropane to said alkylene oxide of 1:1-10; or
(C) the salt of (A) or (B) with an inorganic or organic acid.

4. The compound of claim 3 in the form of its salt with an inorganic or organic acid.

5. The compound of claim 3 wherein said diaminopropane is: N-n-dodecyl-1,3-diaminopropane; N-n-tetradecyl-1,3-diaminopropane; or a mixture thereof.

6. The compound of claim 3 wherein said diaminopropane is a mixture of about 65–75 mol % N-n-dodecyl-1,3-diaminopropane and the balance to 100 mol % of N-n-tetradecyl-1,3-diaminopropane.

7. The compound of claim 3 wherein said glutamic acid ester is at least one of 5-methyl, 5-ethyl, 5-propyl, or 5-butyl.

8. The compound of claim 3 wherein said at least one glutamic acid or its ester is the L-glutamic acid 5-methyl ester.

9. The compound of claim 6 wherein said at least one glutamic acid or its ester is the L-glutamic acid 5-methyl ester.

10. The compound of claim 9 wherein the mol ratio of a:b is about 1:1.

11. The compound of claim 10 wherein said reaction product is alkoxylated with about 1–10 mols of ethylene oxide and/or propylene oxide for each mol of diaminopropane.

12. The compound of claim 10 wherein said reaction product is alkoxylated with about 1 mol of ethylene oxide or propylene oxide for each mol of diaminopropane.

13. The compound of claim 3 in the form of its salt with at least one of hydrochloric, sulfuric, phosphoric, formic, acetic, lactic, tartaric, citric or benzoic acids.

14. The compound of claim 9 in the form of its salt with at least one of hydrochloric, sulfuric, phosphoric, formic, acetic, lactic, tartaric, citric or benzoic acids.

15. The compound of claim 11 in the form of its salt with at least one of hydrochloric, sulfuric, phosphoric, formic, acetic, lactic, tartaric, citric or benzoic acids.

16. A preparation for cleaning, disinfecting and preserving, comprising a liquid, paste, or solid carrier, and a microbistatic and/or microbicidal effective amount of a compound which is
(A) the reaction product of (a) at least one $C_{12-14}$-alkyl N-substituted 1,3-diaminopropane with (b) at least one of glutamic acid or its $C_{1-4}$-alkyl 5-ester in a mol ratio a:b of 1:1-2;

(B) the alkoxylation product of (A) with ethylene oxide or propylene oxide in a mol ratio of said diaminopropane to said alkylene oxide of 1:1–10; or (C) the salt of (A) or (B) with an organic or inorganic acid.

17. The preparation of claim 16 wherein said compound is in the form of its salt with an organic or inorganic acid.

* * * * *